United States Patent [19]

Bielefeldt et al.

[11] Patent Number: 5,145,961
[45] Date of Patent: Sep. 8, 1992

[54] PROCESS FOR THE PREPARATION OF 5-FLUOROPYRIMIDINES

[75] Inventors: Dietmar Bielefeldt, Ratingen; Rudolf Braden, Odenthal, both of Fed. Rep. of Germany

[73] Assignee: Bayer Aktiengesellschaft, Leverkusen, Fed. Rep. of Germany

[21] Appl. No.: 834,906

[22] Filed: Feb. 13, 1992

[30] Foreign Application Priority Data

Feb. 22, 1991 [DE] Fed. Rep. of Germany ....... 4105553

[51] Int. Cl.$^5$ .......................................... C07D 239/30
[52] U.S. Cl. .................................................. 544/334
[58] Field of Search ......................................... 544/334

[56] References Cited

U.S. PATENT DOCUMENTS 3,314,955  4/1967  Boudakian et al. .................. 544/334
4,786,733 11/1988  Van Der Puy et al. ............ 546/286

FOREIGN PATENT DOCUMENTS 647512  1/1985  Switzerland .

OTHER PUBLICATIONS

Journal of Fluorine Chemistry, vol. 25, 1984; pp. 435–446; M. M. Boudakian et al.: 'Substitutive Aromatic Fluorination with Chlorine Pentafluoride', pp. 438, 444.

*Primary Examiner*—John M. Ford
*Attorney, Agent, or Firm*—Sprung Horn Kramer & Woods

[57] ABSTRACT

5-Fluoropyrimidines are obtained in an advantageous manner from halogenated 5-unsubstituted pyrimidines, when these are reacted with elemental fluorine in the presence of a solvent.

8 Claims, No Drawings

PROCESS FOR THE PREPARATION OF 5-FLUOROPYRIMIDINES

The present invention relates to a particularly advantageous process for the preparation of 5-fluoropyrimidines.

It is known that 5-fluoropyrimidines can be prepared by reacting 2,4,6-trifluoropyrimidine with $ClF_5$ (see J. Fluorine Chem. 25, 435 (1984)). Disadvantages of this process are that 5-fluoropyrimidines are always obtained as a mixture with 5-chloropyrimidines, the yield of 5-fluoropyrimidines is low, and that $ClF_5$, because of its particularly strong corrosive properties, is difficult to handle.

The preparation of 5-fluoro-trichloropyrimidine from tetrafluoropyrimidine by back-chlorination using HCl in an autoclave is also known (see J. Fluorine Chem. 45, 417 (1989)). The yields in this case are also low. The method of working with HCl under pressure is particularly laborious.

A process has now been found for the preparation of 5-fluoropyrimidines of the formula (I)

in which
X represents, independently of each other, fluorine or chlorine and
n is 1, 2 or 3,
which is characterised in that a halogenated pyrimidine of the formula (II)

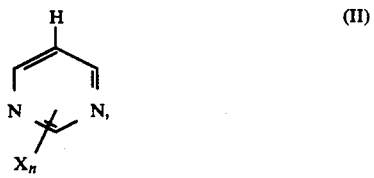

in which
X and n have the meanings defined as for formula (I), is reacted with elemental fluorine in the presence of a solvent.

If pyrimidines of the formula (II) containing only fluorine are used, pure 5-fluoropyrimidines of the formula (I) are obtained directly. If chlorine-containing pyrimidines of the formula (II) are used, mixtures of 5-fluoropyrimidines of the formula (I) containing chlorine and possibly additional fluorine are generally obtained.

Suitable temperatures for carrying out the process according to the invention are for example those in the range −100 to +80° C.

0.2 to 0.5 mol of elemental fluorine can be used, for example, per mole of the halogenated pyrimidine of the formula (II) used. The elemental fluorine can be used as the pure gas, or as a mixture with inert gases, e.g. noble gases or nitrogen. The concentration of fluorine in such a fluorine/inert gas mixture can be for example 0.5 to 99.9% by weight. This concentration is preferably 5 to 50% by weight.

The solvent for the process according to the invention can be for example trichlorofluoromethane, dichlorodifluoromethane, perfluorohexane, perfluorooctane, trifluoroacetic acid or Fomblin ®. Trichlorofluoromethane is preferred.

The halogenated pyrimidines of the formula (II) required as starting materials are commercial products of the Aldrich company or are obtainable according to U.S. Pat. No. 3,314,955.

The mixture present after the reaction can, for example, be worked up by binding the hydrogen fluoride formed to a base, e.g. sodium fluoride, potassium fluoride or basic aluminium oxide, then filtering the mixture, and subjecting the filtrate to a distillation, if required under reduced pressure. The bases can also be added before or during the reaction.

The process according to the invention is generally carried out at atmospheric pressure. If desired, it can also be carried out at elevated or reduced pressure, e.g. 0.1 to 5 bar.

In particular, perhalogenated 5-fluoropyrimidines of the formula (I), i.e. those in which n is 3, may be prepared especially well and simply in the manner according to the invention.

With the aid of the process according to the invention, 5-fluoropyrimidines of the formula (I) can be prepared in good yields, at low temperatures and without use of pressure.

5-Fluoropyrimidines of the formula (I) are important intermediates, for example for the preparation of pharmacologically active substances. Pharmacologically active substances, can be prepared, for example, by catalytic hydrogenation of a 5-fluoropyrimidine derivative of the formula (I) followed by hydrolysis (see J. Fluorine Chem. 45, 417 (1989)).

EXAMPLES

Example 1

0.5 mol of fluorine in the form of a 30% by volume mixture with helium was introduced into a suspension of 29.0 g (0.216 mol) of 2,4,6-trifluoropyrimidine, 21 g of sodium fluoride (0.5 mol) and 250 ml of trichlorofluoromethane at a temperature of −78° C. The rate of introduction was 0.15 mol of fluorine per hour. After the introduction was complete, the reaction mixture was filtered and 21.0 g of tetrafluoropyrimidine (=64% of theory) were obtained from the filtrate by distillation.

Example 2

0.5 mol of fluorine in the form of a 30% by volume mixture with helium was introduced into a suspension of 36.7 g (0.2 mol) of 2,4,6-trichloropyrimidine, 21 g of sodium fluoride (0.5 mol) and 250 ml of trichlorofluoromethane, at a temperature of −78° C. The rate of introduction was 0.15 mol of fluorine per hour. After the introduction, the reaction mixture was filtered and 19.3 g of pure 5-fluoro-2,4,6-trichloropyrimidine were obtained from the filtrate by distillation over iron filings. This corresponds to a yield of 48% of theory. The boiling point of the isolated product was 80°−87° C. at 10 mbar. The reaction mixture also contained more highly fluorinated pyrimidine derivatives.

Example 3

0.55 mol of fluorine in the form of an 18% by volume mixture with helium was introduced into a suspension of 92 g (0.5 mol) of 2,4,6-trichloropyrimidine, 100 g of sodium fluoride and 1000 ml of trichlorofluoromethane, at −78° C. After the introduction was complete, the reaction mixture was filtered and 59.4 g (=59% of theory) of 5-fluoro-2,4,6-trichloropyrimidine were distilled off from the filtrate.

What is claimed is:

1. A process for the preparation of 5-fluoropyrimidines of the formula (I)

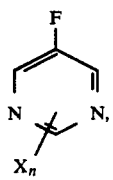
(I)

in which
  X represents independently of each other, fluorine or chlorine and
  n is 1, 2 or 3,
in which a halogenated pyrimidine of the formula (II)

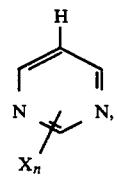
(II)

in which
  X and n have the meanings defined as for formula (I), is reacted with elemental fluorine in the presence of a solvent.

2. The process of claim 1, in which temperatures in the region −100° to +80° C. are employed.

3. The process of claim 1, in which 0.5 to 3 mols of elemental fluorine are used per mole of the halogenated pyrimidine of the formula (II).

4. The process of claim 1, in which the elemental fluorine is used as the pure gas.

5. The process of claim 1, in which the fluorine is used as a mixture with inert gases.

6. The process of claim 1, in which the solvent used is trichlorofluoromethane, dichlorodifluoromethane, perfluorohexane, perfluorooctane, trifluoroacetic acid and/or Fomblin ®.

7. The process of claim 1, in which atmospheric pressure is employed.

8. The process of claim 1, in which the mixture present after the reaction is worked up by binding the hydrogen fluoride formed to a base, then filtering the mixture, and subjecting the filtrate to a distillation.

* * * * *